(12) United States Patent
Bourgerette et al.

(10) Patent No.: US 8,152,977 B2
(45) Date of Patent: Apr. 10, 2012

(54) MULTICHANNEL POTENTIOSTAT HAVING AN ADJUSTABLE COUNTER-ELECTRODE POTENTIAL

(75) Inventors: Alain Bourgerette, Villard Bonnot (FR); Gilles Marchand, Pierre-Chatel (FR)

(73) Assignee: Commissariat a l'Energie Atomique, Paris (FR)

( * ) Notice: Subject to any disclaimer, the term of this patent is extended or adjusted under 35 U.S.C. 154(b) by 601 days.

(21) Appl. No.: 12/285,678

(22) Filed: Oct. 10, 2008

(65) Prior Publication Data

US 2009/0114537 A1    May 7, 2009

(30) Foreign Application Priority Data

Nov. 2, 2007  (FR) ..................... 07 07720

(51) Int. Cl.
*G01N 27/26*  (2006.01)

(52) U.S. Cl. ....................... 204/406; 204/412

(58) Field of Classification Search ............. 204/403.01, 204/403.02, 403.03, 406, 412
See application file for complete search history.

(56) References Cited

U.S. PATENT DOCUMENTS

| 4,315,753 | A | | 2/1982 | Bruckenstein et al. |
| 4,426,621 | A | * | 1/1984 | Galwey et al. ................ 324/439 |
| 2005/0211571 | A1 | | 9/2005 | Schulein et al. |

FOREIGN PATENT DOCUMENTS

EP    0 068 101 A2    1/1983

OTHER PUBLICATIONS

Frey et al., "Design of an Integrated Potentiostat Circuit for CMOS Bio Sensor Chips," *Proceedings of ISCAS*, vol. V, Dec. 31, 2003, pp. 9-12.

* cited by examiner

*Primary Examiner* — Bruce Bell
(74) *Attorney, Agent, or Firm* — Oliff & Berridge, PLC

(57) ABSTRACT

The multichannel potentiostat comprises a reference terminal, a counter-electrode terminal, and at least two working terminals, respectively designed to be connected to a reference electrode, a counter-electrode and at least two working electrodes of an electrochemical cell. The potentiostat comprises first and second regulating circuits to apply a setpoint voltage respectively between the first and second working terminals and the reference terminal. The potentiostat comprises a control circuit of the counter-electrode voltage applied to the counter-electrode terminal. The control circuit comprises a first input terminal connected to a predefined potential and a second input terminal to which a regulating voltage representative of at least one of the voltages of the working terminals is applied.

6 Claims, 2 Drawing Sheets

US 8,152,977 B2

MULTICHANNEL POTENTIOSTAT HAVING AN ADJUSTABLE COUNTER-ELECTRODE POTENTIAL

BACKGROUND OF THE INVENTION

The invention relates to a multichannel potentiostat comprising a reference terminal, a counter-electrode terminal and at least two working terminals respectively designed to be connected to a reference electrode, a counter-electrode and at least two working electrodes of an electrochemical cell, the potentiostat comprising predefined setpoint voltages and first and second regulating circuits to apply setpoint voltages respectively between the first and second working terminal and the reference terminal.

STATE OF THE ART

Electrochemical cells are very commonly used in a wide range of fields of analysis. As a general rule, in an analysis device, an electrochemical cell is associated with a potentiostat which performs two essential functions. It imposes a predefined potential difference, i.e. a setpoint voltage, between a working electrode and a reference electrode of the electrochemical cell. At the same time, the potentiostat measures the current flowing between the working electrode and a counter-electrode of the cell.

Multiple potentiostat architectures exist depending on the complexity of the studies and/or of the phenomena to be analyzed. Single-channel potentiostats associated with a single working electrode and multichannel potentiostats associated with several working electrodes already exist. In the category of multichannel potentiostats, analysis device potentiostats having one reference electrode for each working electrode and analysis device potentiostats having a single reference electrode for several working electrodes can be differentiated, whether the potentiostat is used with one or more electrochemical cells. Within the category of analysis devices having one reference electrode for several working electrodes, a distinction can also be made between devices in which the counter-electrode and reference electrode are combined in the same electrode and devices in which these electrodes are separate.

The article by Frey et al. "Design of an Integrated Potentiostat Circuit for CMOS BIO Sensor Chips", Proceeding of ISCAS, vol. V, 2003, p 9-12, describes the use of a potentiostat associated with two working electrodes, a reference electrode and a counter-electrode. In the corresponding analysis device, the reference electrode voltage is controlled by means of an operational amplifier having an input connected to the reference electrode and an output connected to the counter-electrode, whereas distinct setpoint voltages are imposed for the two working electrodes. Moreover, this device is of limited interest as the setpoint voltages applied to the two working electrodes are necessarily of opposite signs (one is positive whereas the other is negative).

This type of multichannel device with a separate counter-electrode and reference electrode is not able to study complex mechanisms, for example different oxidation reducing species mixed within one and the same electrolyte and able to react with one another. In this type of device, the output voltage range is not optimized with respect to the supply voltage range, which limits their interest.

OBJECT OF THE INVENTION

The object of the invention is to provide a potentiostat that in particular enables cyclic volt-ampere metering to be performed with an optimized available measuring range.

According to the invention, this object is achieved by the fact that the potentiostat comprises a control circuit of the counter-electrode voltage applied to the counter-electrode terminal, said control circuit comprising a first input terminal connected to a preset potential and a second input terminal to which a regulating voltage representative of at least one of the working terminal voltages is applied.

BRIEF DESCRIPTION OF THE DRAWINGS

Other advantages and features will become more clearly apparent from the following description of particular embodiments of the invention given for non-restrictive example purposes only and represented in the accompanying drawings, in which.

DESCRIPTION OF PREFERRED EMBODIMENTS OF THE INVENTION

Figure 1:
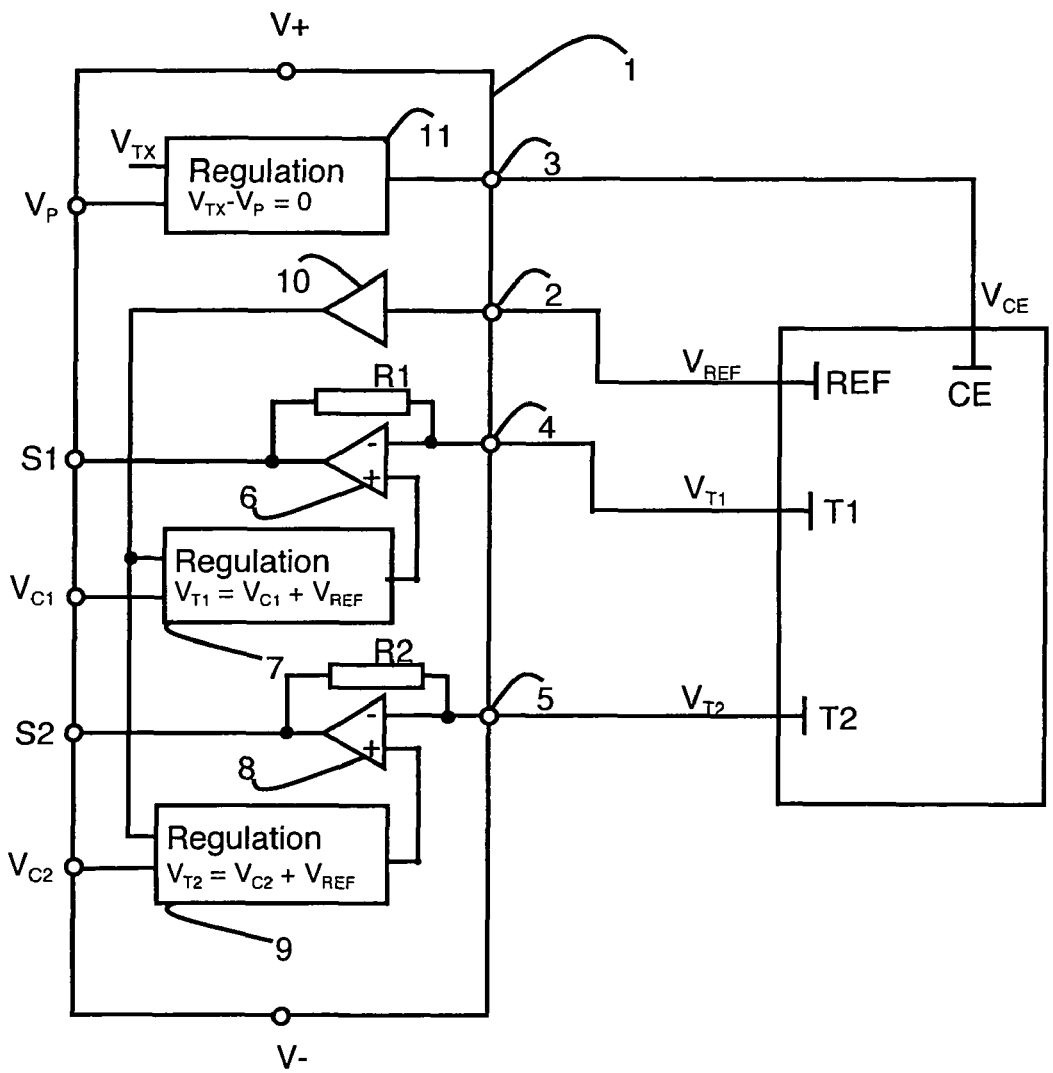
FIG. 1 schematically represents a particular embodiment of a potentiostat according to the invention.

As illustrated in FIG. 1, potentiostat 1 comprises a reference terminal 2, a counter-electrode terminal 3 and at least two working terminals 4 and 5, respectively designed to be connected to a reference electrode REF, a counter-electrode CE and at least two working electrodes T1 and T2 of an electrochemical cell which are all immersed in the same electrolyte. Potentiostat 1 is of multichannel type as it presents several working electrodes for one reference electrode. The potentiostat is supplied by supply voltages V+ and V−.

In conventional manner, the reference electrode is adjusted to a reference potential $V_{REF}$, each working electrode is adjusted to a different working potential, respectively $V_{T1}$ and $V_{T2}$, and the counter-electrode is adjusted to a counter-electrode potential $V_{CE}$.

Potentiostat 1 enables a predefined setpoint voltage, respectively first $V_{C1}$ and second $V_{C2}$, to be applied between one of working terminals 4, 5 and reference terminal 2. Each working electrode therefore has a working potential ($V_{T1}$, $V_{T2}$) that is proper to it and which depends on the setpoint voltage that is assigned thereto and on the reference electrode potential.

Reference terminal 2 is preferably connected by means of a follower assembly 10 to a first input terminal of two regulating circuits 7 and 9, respectively associated with working terminals 4 and 5. Each regulating circuit also has a second input terminal connected to a corresponding setpoint terminal to which the associated setpoint voltage $V_{C1}$, or $V_{C2}$ is applied. Regulating circuits 7, 9 thereby enable a predefined setpoint voltage, $V_{C1}$ or $V_{C2}$, to be applied between each working terminal 4, 5 and the reference terminal such that:

$$V_{T1} = V_{C1} + V_{REF}$$

$$V_{T2} = V_{C2} + V_{REF}$$

In the particular embodiment illustrated in FIG. 1, the inverting input of a first measuring operational amplifier 6 is connected to working terminal 4 and, via a resistor R1, to the output of operational amplifier 6, which is connected to a first measuring output S1 of the potentiostat. The non-inverting input of operational amplifier 6 is connected to the output of first regulating circuit 7.

In the same way, the inverting input of a second measuring operational amplifier 8 is connected to working terminal 5 and, via a resistor R2, to the output of operational amplifier 8, which is connected to a second measuring output S2 of the potentiostat. The non-inverting input of operational amplifier 8 is connected to the output of second regulating circuit 9.

This assembly therefore enables the potentials of the two working electrodes (T1, T2) to be set independently from one another so that the potential difference between one of the working electrodes and the reference electrode is determined by the corresponding setpoint voltage ($V_{C1}$, $V_{C2}$). The setpoint voltages ($V_{C1}$, $V_{C2}$) are therefore independent from one another.

This assembly further enables signals representative of the value of the currents flowing in the two working electrodes (T1, T2) to be obtained on measuring outputs S1 and S2. The maximum (VSmax) and minimum (VSmin) voltages that can be obtained on outputs S1 and S2 define the measuring range VSmax-VSmin for each of the outputs.

Potentiostat 1 also enables the counter-electrode potential $V_{CE}$ to be set, via a counter-electrode voltage control circuit 11, so as to adjust for example the potential of a working electrode or the mean of the working electrode potentials to a preset potential $V_P$. It is thus possible to vary the potential of working terminals 4, 5 and therefore of working electrodes $V_{T1}$, $V_{T2}$ by means of the counter-electrode, thereby increasing the measuring range. The potential $V_P$ can for example be ground or advantageously the mean of the potentiostat supply voltages, or even more advantageously the mean of the limit voltages of the electrochemical window of the electrolyte. The preset potential $V_P$ can moreover also be a potential that is fixed by means of an additional terminal of potentiostat 1 in the same way as for potentials $V_{C1}$ and $V_{C2}$.

Counter-electrode potential $V_{CE}$, associated with counter-electrode terminal 3 is fixed by the output of control circuit 11, which comprises a first input terminal connected to the potential $V_P$ and a second input terminal to which a regulating voltage $V_{TX}$ representative of at least one of the voltages ($V_{T1}$, $V_{T2}$) of working terminals (4, 5) is applied. Regulating voltage $V_{TX}$ can be constituted by a voltage applied to a working terminal or a combination of the different voltages applied to the working terminals, for example the mean of the voltages applied to the working terminals. Control circuit 11 regulates the counter-electrode voltage $V_{CE}$ so that $V_{TX}-V_P=0$. Practically, control circuit 11 has a first input terminal connected to potential $V_P$ and a second input terminal connected to the output of at least one of regulating circuits 7 and 9. Preset potential $V_P$ is therefore a potential towards which the potential of a working electrode or of a combination of the working electrode potentials, for example the mean of the working electrode potentials, is maintained by controlling the counter-electrode potential $V_{CE}$.

Figure 2:
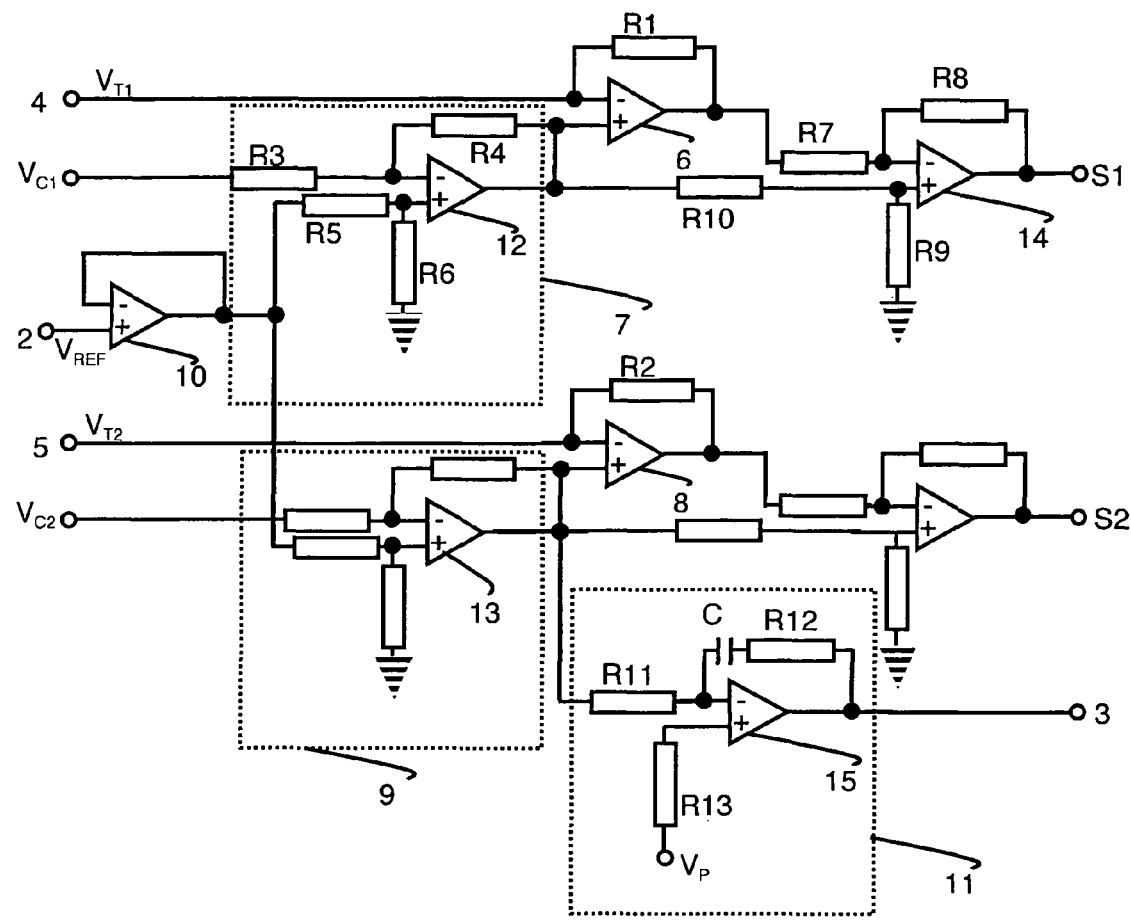
FIG. 2 represents a particular embodiment of a potentiostat according to the invention in greater detail.

In a first alternative embodiment, it can be sought to make the potential of second working electrode T2 tend to the potential $V_P$ ($V_{T2}-V_P=0$). The regulating voltage $V_{TX}$ is then constituted by working voltage $V_{T2}$ applied to associated working terminal 5. In this way, counter-electrode potential $V_{CE}$ is modulated so that the potential of second working electrode $V_{T2}$ tends to the potential $V_P$. Practically, the second terminal of control circuit 11 is then preferably connected to the output of regulating circuit 9 (FIG. 2).

In like manner, in a second alternative embodiment, it can be sought to make the potential of first working electrode T1 tend to the potential $V_P$ ($V_{T1}-V_P=0$). Regulating voltage $V_{TX}$ is then formed by working voltage $V_{T1}$ applied to the associated working terminal 4. In this way, counter-electrode potential $V_{CE}$ is modulated so that the potential of first working electrode $V_{T1}$ tends to the potential $V_P$. Practically, the second terminal of control circuit 11 is then preferably connected to the output of regulating circuit 7.

In a third alternative embodiment, it can be sought to set the potential $V_P$ equipotentially between the potentials of working terminals 4, 5. Regulating voltage $V_{TX}$ is then constituted by the mean of voltages $V_{T1}$ and $V_{T2}$ applied to working terminals 4 and 5.

In practice, the second terminal of control circuit 11 is advantageously connected to the output of the regulating circuit or circuits 7, 9 associated with the electrode or with the plurality of electrodes whose potential is to be made to tend to the potential $V_P$.

As illustrated in FIG. 2, each regulating circuit 7, 9 advantageously comprises an operational amplifier 12, 13 connected as a summer. In the particular embodiment illustrated in FIG. 2, the inverting input of operational amplifier 12 is connected to the corresponding setpoint terminal ($V_{C1}$) via a resistor R3 and to the output of operational amplifier 12 by a resistor R4. The non-inverting input of operational amplifier 12 is connected via a resistor R5 to the output of the follower assembly 10 connected to reference terminal 2, and is grounded via a resistor R6. The potential applied to the output of operational amplifier 12, i.e. to the output of regulating circuit 7, is therefore a function of the reference potential $V_{REF}$ and of the corresponding setpoint voltage $V_{C1}$.

In like manner, the assembly of regulating circuit 9 enables the potential $V_{T2}$ of corresponding working electrode T2 to be set as a function of the corresponding setpoint voltage $V_{C2}$.

Furthermore, in FIG. 2, the output of operational amplifier 6 is advantageously connected via a resistor R7 to the inverting input terminal of an operational amplifier 14, which is feedback connected by means of a resistor R8 and whose output is connected to measuring output S1. Resistor R8 thereby connects the inverting input and the output of operational amplifier 14. The non-inverting input of operational amplifier 14 is grounded via a resistor R9, and is connected to the output of operational amplifier 12 via a resistor R10. Operational amplifier 14 thereby enables a voltage representative of the current value flowing through working electrode T1 to be obtained on measuring output S1.

A similar assembly can be performed from outputs of operational amplifiers 8 and 13 to obtain a voltage representative of the current value flowing through working electrode T2 on measuring output S2.

In the particular embodiment illustrated in FIG. 2, control circuit 11 of counter-electrode voltage $V_{CE}$ comprises an operational amplifier 15 that has an inverting input connected to the output of operational amplifier 13 via a resistor R11. This inverting input is also connected to the output of operational amplifier 15 via a resistor R12 and capacitor C connected in series. The non-inverting input of operational amplifier 15 is connected to the potential $V_P$ by a resistor R13. Control circuit 11 of counter-electrode voltage is thereby formed by an operational amplifier 15 having an inverting input that constitutes the second input terminal of control circuit 11 and a non-inverting input that constitutes the first input terminal of control circuit 11. In this particular embodiment, the regulating voltage $V_{TX}$ is constituted by the working voltage $V_{T2}$ applied to working terminal 5, and the counter-electrode potential $V_{CE}$ is set such as to make the potential of second working electrode $V_{T2}$ tend to the potential $V_P$ ($V_{T2}-V_P=0$).

In an alternative embodiment, not represented, to make the potential of first working electrode $V_{T1}$ tend to the potential $V_P$ ($V_{T1}-V_P=0$), the inverting input of operational amplifier 15 is connected to the output of operational amplifier 12.

In a third alternative embodiment, not represented, the outputs of operational amplifiers 12 and 13 are connected to the inputs of a summer having its output connected to the inverting input of operational amplifier 15. In this case $V_{TX}=(V_{T1}+V_{T2})/2$. Counter-electrode potential $V_{CE}$ is then set such as to place the potential $V_P$ equipotentially between the potentials of the two working electrodes T1 and T2.

In this way, the potentiostat according to the invention enables the counter-electrode potential to be controlled thereby optimizing the output voltage range with respect to the supply voltages range of the potentiostat. This approach can be particularly interesting if a constraint exists on the supply voltages.

The potentiostat further enables independent setpoint voltages to be applied between the working electrodes and the reference electrode, which means that a positive setpoint voltage between a working electrode and the reference electrode and a negative setpoint voltage between another working electrode and the reference electrode can be applied simultaneously.

The invention claimed is:

1. A multichannel potentiostat comprising:
   a reference terminal, a counter-electrode terminal and at least two working terminals respectively designed to be connected to a reference electrode, a counter-electrode and at least two working electrodes of an electrochemical cell,
   a first regulating circuit having a first input electrically linked to the reference terminal and a second input electrically linked to a first working terminal, the first regulating circuit being configured to apply a first setpoint voltage between the reference terminal and the first working terminal,
   a second regulating circuit having a first input electrically linked to the reference terminal and a second input electrically linked to the second working terminal, the second regulating circuit being configured to apply a second setpoint voltage between the reference terminal and the second working terminal,
   a control circuit of the counter-electrode voltage applied to the counter-electrode terminal, wherein a first input terminal of the control circuit is linked to an output of the first regulating circuit and wherein a second input terminal of the control circuit is designed to be linked to a first device providing a first voltage on the second input, the control circuit being configured to apply a third setpoint voltage between the first voltage and the first setpoint voltage by modulating the counter-electrode voltage.

2. The potentiostat according to claim 1, wherein the first input terminal of the control circuit is linked to an output of the second regulating circuit.

3. The potentiostat according to claim 1, wherein the first input terminal of the control circuit is connected to a circuitry configured to provide an average of a voltage provided by the output of the first regulating circuit and a voltage provided by an output of the second regulating circuit.

4. The potentiostat according to claim 1, wherein the first input terminal of the control circuit is connected to the first working terminals.

5. The potentiostat according to claim 1, wherein the inputs electrically linked to the first and second working terminals of the regulating circuits are connected to inputs of a first and a second measuring operational amplifier, respectively, which have second inputs connected to the corresponding working terminal.

6. The potentiostat according to claim 5, wherein the counter-electrode voltage control circuit is formed by an operational amplifier having an inverting input forming the first input terminal of the control circuit and a non-inverting input forming a second input terminal of the control circuit.

* * * * *